(12) United States Patent
Denis et al.

(10) Patent No.: US 8,075,604 B2
(45) Date of Patent: Dec. 13, 2011

(54) MULTI-THREAD BONE SCREW AND METHOD

(75) Inventors: Francis Denis, Minneapolis, MN (US);
Timothy A. Garvey, Edina, MN (US);
Joseph H. Perra, Shoreview, MN (US);
Manuel Pinto, Minnetonka, MN (US);
James D. Schwender, Edina, MN (US);
Ensor Transfeldt, Edina, MN (US);
Michael S. Veldman, Memphis, TN (US); William A. Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 924 days.

(21) Appl. No.: 11/355,877

(22) Filed: Feb. 16, 2006

(65) Prior Publication Data

US 2007/0233122 A1    Oct. 4, 2007

(51) Int. Cl.
*A61B 17/04* (2006.01)
*A61B 17/86* (2006.01)
*A61F 2/08* (2006.01)

(52) U.S. Cl. .................................................. 606/315

(58) Field of Classification Search ............ 606/61, 606/69, 73, 65, 104, 264, 288, 275, 60, 289, 606/300, 301, 315, 316, 317, 309, 319
See application file for complete search history.

(56) References Cited

U.S. PATENT DOCUMENTS

| | | | |
|---|---|---|---|
| RE28,111 E | | 8/1974 | Laverty |
| 3,861,269 A | | 1/1975 | Laverty |
| 4,844,676 A | | 7/1989 | Adamek |
| 5,120,171 A | * | 6/1992 | Lasner ........................ 411/308 |
| 5,259,398 A | | 11/1993 | Vrespa |
| 5,385,439 A | | 1/1995 | Hurdle |
| 5,395,371 A | | 3/1995 | Miller et al. |
| 5,409,486 A | | 4/1995 | Reese |
| 5,520,688 A | | 5/1996 | Lin |
| 5,540,690 A | | 7/1996 | Miller et al. |
| 5,545,163 A | | 8/1996 | Miller et al. |
| 5,601,553 A | * | 2/1997 | Trebing et al. ............. 606/86 B |
| 5,607,428 A | | 3/1997 | Lin |
| 5,613,968 A | | 3/1997 | Lin |
| 5,643,263 A | | 7/1997 | Simonson |
| 5,779,417 A | | 7/1998 | Barth et al. |
| 5,814,046 A | | 9/1998 | Hopf |
| 5,947,967 A | | 9/1999 | Barker |

(Continued)

FOREIGN PATENT DOCUMENTS

EP        0 241 792 A1      10/1987

(Continued)

*Primary Examiner* — Thomas C. Barrett
*Assistant Examiner* — Sameh Boles (57) ABSTRACT

A bone screw comprising a threaded shank including a distal end portion and a proximal end portion, and defining a first threaded section extending from the distal end portion toward the proximal end portion and adapted for anchoring in cancellous bone, and a second threaded section extending contiguously from the first threaded section toward the proximal end portion and adapted for engagement in cortical bone, with the second threaded section having a finer thread pattern relative to the first threaded section. In one embodiment, the first threaded section includes a first helical threading defining a single lead thread pattern for anchoring in cancellous bone, and the second threaded section includes a second helical threading interleaved with the first threading to define a duel lead thread pattern for engagement in cortical bone. In a further embodiment, the bone screw includes a head portion extending from the threaded shank and configured for coupling to a spinal implant.

40 Claims, 5 Drawing Sheets

U.S. PATENT DOCUMENTS

| | | | |
|---|---|---|---|
| 5,964,768 A * | 10/1999 | Huebner | 606/317 |
| 6,030,162 A * | 2/2000 | Huebner | 411/413 |
| 6,045,312 A | 4/2000 | Hsing | |
| 6,086,303 A | 7/2000 | Fluckiger | |
| 6,116,832 A | 9/2000 | Wolf et al. | |
| 6,129,730 A | 10/2000 | Bono et al. | |
| 6,224,602 B1 | 5/2001 | Hayes | |
| 6,368,319 B1 | 4/2002 | Schaefer | |
| 6,471,703 B1 | 10/2002 | Ashman | |
| 6,585,740 B2 * | 7/2003 | Schlapfer et al. | 606/308 |
| 6,602,256 B1 | 8/2003 | Hayes | |
| 6,984,235 B2 * | 1/2006 | Huebner | 470/10 |
| 7,270,665 B2 * | 9/2007 | Morrison et al. | 606/300 |
| 7,559,846 B2 | 7/2009 | Ferrell | |
| 2002/0016594 A1 | 2/2002 | Schlapfer et al. | |
| 2003/0026675 A1 | 2/2003 | McGovern et al. | |
| 2003/0153911 A1 | 8/2003 | Shluzas | |
| 2004/0141827 A1 | 7/2004 | Dicke | |
| 2004/0172031 A1 | 9/2004 | Rubecamp et al. | |
| 2004/0210227 A1 | 10/2004 | Trail et al. | |
| 2008/0249579 A1 | 10/2008 | Taylor | |
| 2009/0062868 A1 | 3/2009 | Casutt | |

FOREIGN PATENT DOCUMENTS

| | | |
|---|---|---|
| FR | 2 789 293 | 8/2000 |
| WO | WO 94/01048 | 1/1994 |
| WO | WO 02/09601 | 2/2002 |
| WO | WO 03/032863 | 4/2003 |
| WO | WO 2006/105935 | 10/2006 |

* cited by examiner

MULTI-THREAD BONE SCREW AND METHOD

FIELD OF THE INVENTION

The present invention relates generally to the field of bone screws, and more particularly relates to a bone screw having multiple threaded sections adapted for engagement with different regions of bone, and a method for using the same.

BACKGROUND

Figure 1:
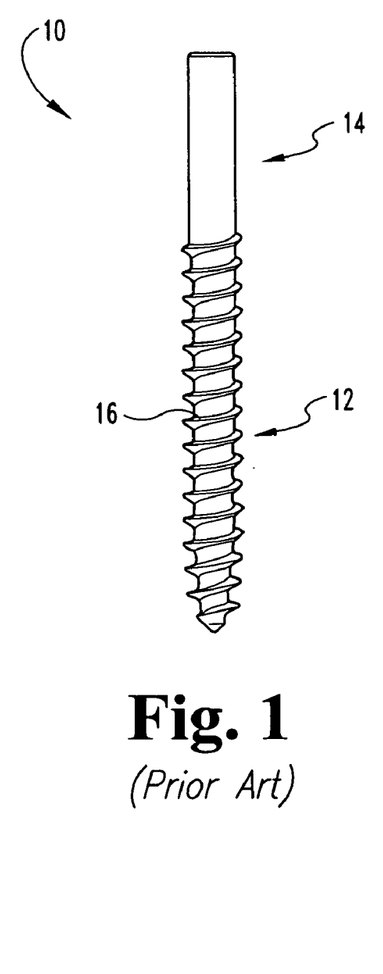
FIG. 1 is an elevational side view of a prior art bone screw.

Various types of fasteners are used to engage implants and other devices to bone. In the spinal field, bone screws are commonly used to attach plates, rods and other types of implants and devices to one or more vertebrae. Referring to FIG. 1, shown therein is a prior art bone screw 10 including a threaded shank portion 12 adapted for engagement in bone, and a head portion 14 for coupling to an elongate member (not shown), such as a spinal rod, via a connector mechanism (not shown). Examples of connector mechanisms suitable for coupling a spinal rod to the head portion 14 of the bone screw 10 are illustrated and described, for example, in U.S. Pat. No. 5,643,263 to Simonson, U.S. Pat. No. 5,947,967 to Barker and U.S. Pat. No. 6,471,703 to Ashman.

The threaded shank portion 12 of the bone screw includes a single, constant pitch threading 16. The threading 16 comprises a relatively wide pitch that is particularly suitable for engagement or purchase within cancellous bone, such as the cancellous bone within the interior region of a vertebral body. Although the threading 16 may be provided with finer pitched threads to increase stability within the relatively harder and denser cortical region of the bone, finer pitched threads tend to decrease purchase within the cancellous region of the bone. Furthermore, finer pitched threads require additional turns to fully engage the bone screw within the bone.

Thus, there remains a need for an improved bone screw and a method for using the same. The present invention satisfies this need and provides other benefits and advantages in a novel and unobvious manner.

SUMMARY

The present invention relates generally to a bone screw having multiple threaded sections adapted for engagement with different regions of bone, and a method for using the same. While the actual nature of the invention covered herein can only be determined with reference to the claims appended hereto, certain forms of the invention that are characteristic of the preferred embodiments disclosed herein are described briefly as follows.

In one form of the present invention, a bone screw is provided having a threaded shank including a distal end portion and a proximal end portion, with the threaded shank defining a first threaded section extending from the distal end portion toward the proximal end portion and adapted for anchoring in cancellous bone, and with the threaded shank defining a second threaded section extending contiguously from the first threaded section toward the proximal end portion and adapted for engagement in cortical bone, and wherein the second threaded section comprises a finer thread pattern relative to the first threaded section.

In another form of the present invention, a spinal system is provided including a bone screw with a threaded shank having a distal end portion and a proximal end portion and a head portion extending from the proximal end portion of the threaded shank, with the threaded shank defining a first threaded section extending from the distal end portion toward the proximal end portion and adapted for anchoring in cancellous bone, and with the threaded shank defining a second threaded section extending contiguously from the first threaded section toward the proximal end portion and adapted for engagement in cortical bone, and wherein the second threaded section comprises a finer thread pattern relative to the first threaded section. The spinal system further includes a spinal implant coupled to the head portion of the bone screw.

In a further form of the present invention, a bone screw is provided having a threaded shank including a distal end portion and a proximal end portion, with the threaded shank including a first helical threading extending from the distal end portion toward the proximal end portion and defining a single lead thread pattern adapted for anchoring in cancellous bone, and with the threaded shank including a second helical threading interleaved with the first threading to define a duel lead thread pattern adjacent the proximal end portion of the threaded shank adapted for engagement in cortical bone.

In still another form of the present invention, a method is provided for engaging a bone screw to a bone having an inner cancellous region and an outer cortical bone region. The method includes the step of providing a bone screw having a threaded shank including a distal end portion and a proximal end portion, with the threaded shank defining a first threaded section extending from the distal end portion toward the proximal end portion and adapted for anchoring in cancellous bone, and with the threaded shank defining a second threaded section extending contiguously from the first threaded section toward the proximal end portion and adapted for engagement in cortical bone, and wherein the second threaded section comprises a finer thread pattern relative to the first threaded section. The method further includes the steps of engaging the first threaded section within the inner cancellous region of the bone, and engaging the second threaded section within the outer cortical region of the bone.

It is one object of the present invention to provide an improved bone screw and a method for using the same. Further objects, features, advantages, benefits, and aspects of the present invention will become apparent from the drawings and description contained herein.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended, and that alterations and further modifications to the illustrated devices and/or further applications of the principles of the invention as illustrated herein are contemplated as would normally occur to one skilled in the art to which the invention relates.

Figure 2:
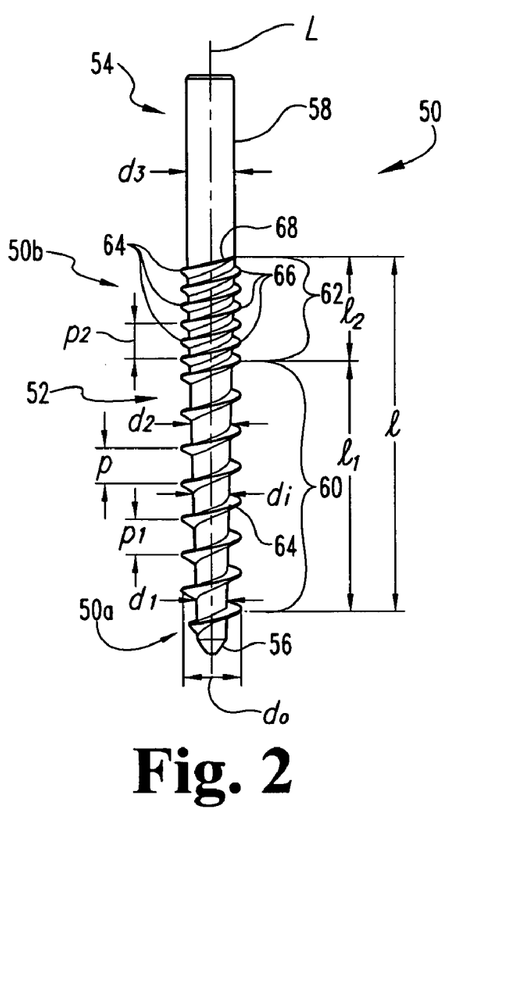
FIG. 2 is an elevational side view of a bone screw according to one form of the present invention.

Referring to FIG. 2, shown therein is a bone screw 50 according to one form of the present invention. The bone screw 50 extends along a longitudinal axis L and includes a distal end portion 50a and a proximal end portion 50b. The bone screw 50 generally includes a threaded shank portion 52 adapted for engagement within bone, and a head portion 54 adapted for coupling with an implant, further details of which will be set forth below. The bone screw 50 may be formed of any suitable biocompatible material such as, for example, titanium, a titanium alloy, stainless steel, metallic alloys, or other materials known to those of skill in the art that possess the mechanical and biocompatible properties suitable for implantation within the body and attachment to bone.

In one embodiment, the threaded shank 52 includes a distal tip 56 that is configured to penetrate bone. In the illustrated embodiment, the distal tip 56 is tapered or pointed to facilitate entry into bone. However, in other embodiments, the distal tip 56 may define a blunt or rounded end. In further embodiments, the distal tip 56 or other portions of the distal end portion 50a may be provided with one or more cutting edges or flutes (not shown) to provide the bone screw 50 with self-cutting or self-tapping capabilities. In still other embodiments, the bone screw 50 may be provided with an axial passage (not shown) extending from the proximal end portion 50b and partially or entirely therethrough to define a cannulation opening, and may be further provided with transverse passages that communicate with the axial passage to define fenestration openings. The cannulation and fenestration openings may be used to deliver material such as, for example, bone cement from the proximal end portion 50b of the bone screw 50 and into areas of the bone axially or laterally adjacent the distal end portion 50a or other portions of the threaded shank 52.

In the illustrated embodiment, the head portion 54 comprises a relatively smooth shaft or stem 58 configured to slidably receive an implant member or a connector for coupling to an implant member. However, it should be understood that other types and configuration of screw head portions 54 are also contemplated, several examples of which will be discussed below. Additionally, bone screw embodiments are also contemplated which do not include a screw head portion. The bone screw 50, and particularly the screw head portion 54, preferably includes features that allow for releasable engagement with a driving tool or instrument (not shown) such as, for example, a screwdriver. In one embodiment, the screw head portion 54 may define a cavity or recess (not shown) sized and shaped to receive a distal end portion of a driver tool. The cavity or recess is preferably non-circular such as, for example, hexagonal or rectangular shaped to provide non-rotational engagement between the head portion 54 and the driver tool to facilitate driving engagement of the bone screw 50 into bone. Alternatively, the screw head portion 54 may define external surface features for engagement by the distal end portion of a driver tool.

The threaded shank 52 has an overall length l and defines a first threaded section 60 extending along a first shank length $l_1$ from the distal end portion 50a toward the proximal end portion 50b, and a second threaded section 62 extending contiguously from the first threaded section 60 to the proximal end portion 50b along a second shank length $l_2$. As will be discussed in greater detail below, the first threaded section 60 includes a first threading 64 that is adapted for anchoring in the cancellous region of a bone, and the second threaded section 62 includes a relatively finer threading 66 that is adapted for anchoring in the cortical region of the bone. Additionally, the second threaded section 62 may define a thread run out 68 adjacent the proximal end portion 50b of the threaded shank 52.

In one embodiment, the length $l_1$ of the first threaded section 60 extends along at least about one half of the overall length l of the threaded shank 52, with the length $l_2$ of the second threaded section 62 extending along the remainder of the overall shank length l. In another embodiment, the length $l_1$ of the first threaded section 60 extends along at least about two-thirds of the overall length l of the threaded shank 52, with the length $l_2$ of the second threaded section 62 extending along the remainder of the overall shank length l. In a further embodiment, the length $l_1$ of the first threaded section 60 extends along at least about three-quarters of the overall length l of the threaded shank 52, with the length $l_2$ of the second threaded section 62 extending along the remainder of the overall shank length l. However, it should be understood that other lengths $l_1$ of the first threaded section 60 relative to the overall length l of the threaded shank 52 are also contemplated as falling within the scope of the present invention.

As should be appreciated, the particular ratio between the shank lengths $l_1$, $l_2$ associated with the first and second threaded sections 60, 62 should preferably be selected based on the characteristics of the bone to which the bone screw 50 is to be engaged. As discussed above, the first threaded section 60 includes thread features that are particularly suited for anchoring in the cancellous region of bone, and the second threaded section 62 includes thread features that are particularly suited for anchoring in the cortical region of bone. In order to maximize the anchoring effectiveness of the bone screw 50, the lengths $l_1$, $l_2$ of the first and second threaded sections should preferably correspond to the desired anchoring depth within the cancellous region of bone and the thickness of the cortical region of bone, respectively.

In the illustrated embodiment of the invention, the first threading 64 includes a single lead in the form of a helical thread pattern which defines the first threaded section 60, and the second threading 66 cooperates with the first threading 64 to provide a dual lead in the form of double helical thread pattern which defines the second threaded section 62. In the illustrated embodiment, the first and second threadings or leads 64, 66 are provided in the form of a helix that extends substantially continuously about the longitudinal axis L and along the length of the shank portion 52. Because the second threading 66 is preferably uniformly and centrally offset relative to the first threading 64, the threadings 64, 66 appear to spiral together along the length $l_2$ of the second threaded section 62 as a continuous thread, but which in actuality comprise separate threadings. As will be discussed below, providing separate threadings along the second threaded section 62 allows the thread pitch associated with each of the first and second threaded sections 60 and 62 to be equal if so desired.

In one specific embodiment, the first threading 64 has a first thread pitch $p_1$, and the second threading 66 is interleaved with the first threading 64 and has a second thread pitch $p_2$ that is substantially equal to the first thread pitch $p_1$. As should be appreciated, since the first and second threadings 64, 66 cooperate with one another to provide a dual lead thread defining the second threaded section 62, and since the first and second threadings 64, 66 have a substantially equal thread pitch p, engagement of the second threaded section 62 into bone will not require any additional turns relative to the first threaded section 60. Additionally, in the illustrated embodiment, the second threading 66 is offset about 180 degrees relative to the first threading 64 such that the turns of the second threading 66 are substantially centered between adjacent turns of the first threading 64. Although a specific thread configuration and arrangement has been illustrated with regard to the bone screw 50, it should be understood that other configurations and arrangements of threadings are also contemplated for use in association with the present invention.

As should be appreciated, providing the first threading 64 with a single lead thread having a relatively large thread pitch tends to increase cancellous bone purchase capabilities, while at the same time maintaining the strength and structural integrity of the cancellous bone. Additionally, providing the second threading 66 with a dual lead thread provides increased fixation strength and stability within the relatively harder and denser cortical bone. Moreover, as indicated above, providing the second threaded section 62 with a dual lead thread having the same thread pitch p as the first threaded section 60 will not require any additional turns of the bone screw 50 for engagement within cortical bone as compared to engagement of the first threaded section 60 within cancellous bone.

In another aspect of the invention, the first and second threaded sections 60, 62 define an inner thread root diameter $d_i$ that varies between the distal end portion 50a and the proximal end portion 50b. In one embodiment, the inner thread root diameter $d_1$ increases from a first root diameter $d_1$ adjacent the distal end portion 50a, to a larger second root diameter $d_2$ adjacent a mid-section of the threaded shank 52, to an even larger third root diameter $d_3$ adjacent the proximal end portion 50b. In another embodiment, the inner thread root diameter $d_i$ increases uniformly between the root diameter $d_1$ adjacent the distal end portion 50a and the root diameter $d_3$ adjacent the proximal end portion 50b. In a further embodiment, the inner thread root diameter $d_i$ increases along substantially the entire length l of the threaded shank 52 between the distal end portion 50a and the proximal end portion 50b. In one specific embodiment, the inner thread root diameter $d_i$ increases by at least about 15% between the root diameter $d_1$ adjacent the distal end portion 50a and the root diameter $d_3$ adjacent the proximal end portion 50b. In another specific embodiment, the inner thread root diameter $d_i$ increases by at least about 25% between the root diameter $d_1$ and the root diameter $d_3$. In a further specific embodiment, the inner thread root diameter $d_i$ increases by at least about 50% between the root diameter $d_1$ and the diameter $d_3$.

As should be appreciated, increasing the inner thread root diameter $d_i$ from the distal end portion 50a toward the proximal end portion 50b, results in a decrease or reduction in the depth of the first and second threadings 64, 66 (as measured from the thread root diameter to the outer thread diameter) from the distal end portion 50a toward the proximal end portion 50b. It should further be appreciated that providing the first threading 64 with a relatively large thread depth (or a relatively small root diameter $d_i$) provides increased cancellous bone purchase capabilities and desirable pullout characteristics compared to the smaller thread depth associated with the second threading 66. Additionally, providing the second threading 66 with a reduced thread depth (or a relatively larger inner thread root diameter $d_i$) relative to the first threading 64 provides increased fixation strength and stability, which is particularly advantageous for fixation within the relatively harder and denser cortical bone, and also tends to reduce resistance to threading engagement within the cortical bone. In one specific embodiment, the thread depth of the first and second threadings 64, 66 decreases by at least about 50% from the distal end portion 50a toward the proximal end portion 50b. As should be appreciated, the thread depth of the threadings 64, 66 is maximized along the first threaded section 60, and particularly adjacent the distal end portion 50a, to provided increased cancellous bone purchase capabilities and desirable pullout characteristics.

In another aspect of the invention, the first and second threaded sections 60, 62 define a substantially uniform outer thread diameter $d_o$ between the distal end portion 50a and the proximal end portion 50b. In one specific embodiment, the outer thread diameter $d_o$ is at least about 15% greater than the inner thread root diameter $d_i$ adjacent the distal end portion 50a. In another specific embodiment, the outer thread diameter $d_o$ is at least about 25% greater than the inner thread root diameter $d_i$ adjacent the distal end portion 50a. In a further specific embodiment, the outer thread diameter $d_o$ is at least about 50% greater than the inner thread root diameter $d_i$ adjacent the distal end portion 50a. As should be appreciated, a larger variation between the outer thread diameter $d_o$ and the inner thread root diameter $d_i$ tends to increase bone purchase capabilities, which is particularly suitable along the first threaded section 60 that is engaged in cancellous bone.

In a further aspect of the invention, the thread pitch p adjacent the distal end portion 50a is equal to or greater than the inner thread root diameter $d_i$ adjacent the distal end portion 50a. In one embodiment, the thread pitch p is equal to or greater than the inner thread root diameter $d_i$ along substantially the entire length $l_1$ of the first threaded section 60 of the threaded shank 52. In another embodiment, the thread pitch p is equal to or greater than the inner thread root diameter $d_i$ along substantially the entire overall length l of the threaded shank 52.

Figure 3:
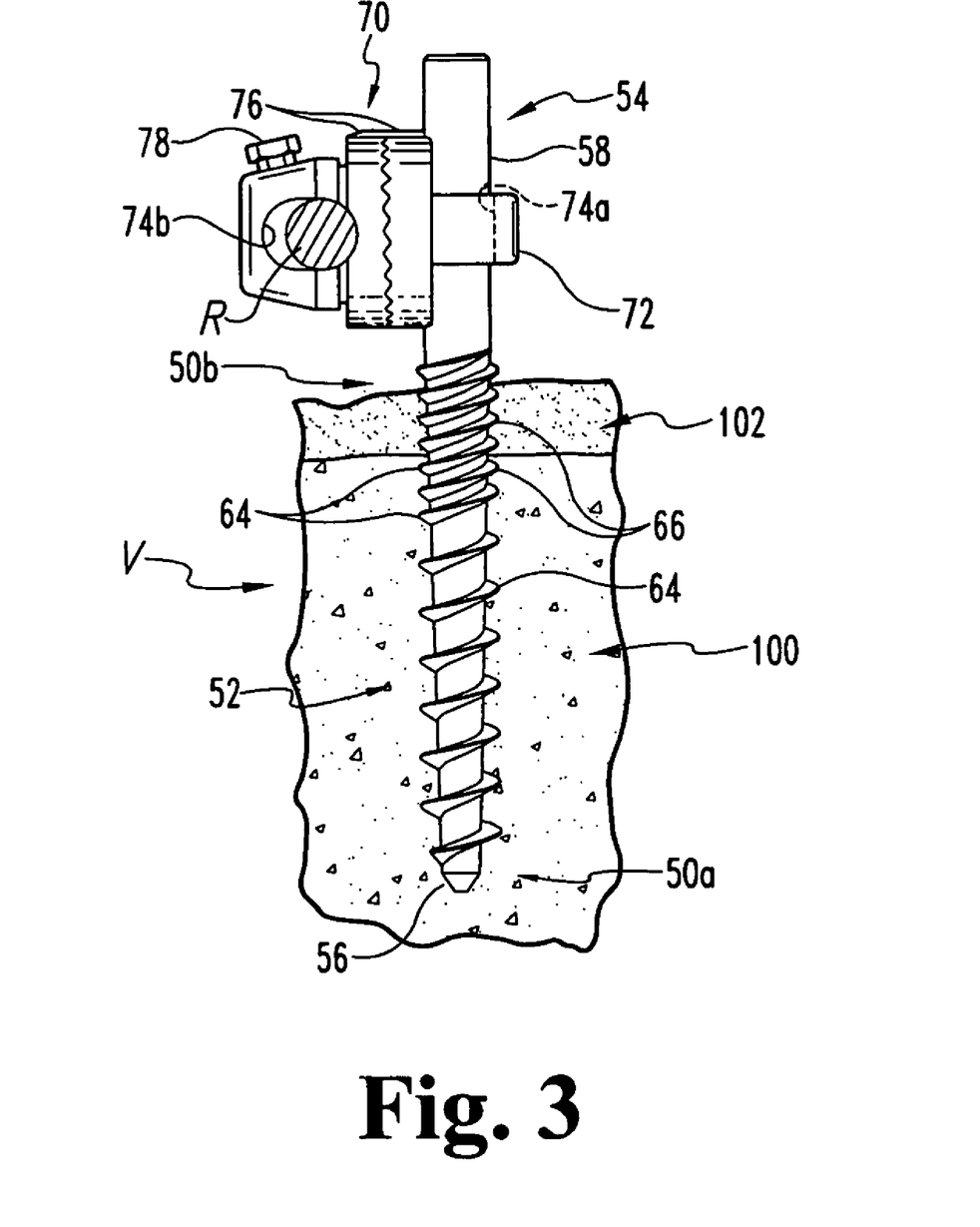
FIG. 3 is an elevational side view of the bone screw illustrated in FIG. 2, as engaged to bone and as coupled to a spinal rod.

As indicated above, the head portion 54 of the bone screw 50 is preferably adapted for coupling with an implant. As illustrated in FIG. 3, in one embodiment, the screw head portion 54 comprises an unthreaded stem portion or shaft 58, and the implant comprises an elongate spinal rod R that is coupled to the screw head 54 via a connector mechanism 70. The connector mechanism 70 includes a connector body 72 defining a first passage 74a for receiving the stem portion 58 of the screw head 54, and a second passage 74b for receiving the spinal rod R. An interface member 76 may be positioned between the spinal rod R and the stem portion 58, and a fastener or set screw 78 is threaded through an opening in the connector body 72 and into contact with the spinal rod R, which in turn engages the interface member 76 with the stem portion 58 of the screw head 54 to fix the angular relationship between the spinal rod R and the bone screw 50. Further details regarding the connector mechanism 70 and other types of connector mechanisms are illustrated and described, for example, in U.S. Pat. No. 5,643,263 to Simonson, U.S. Pat. No. 5,947,967 to Barker and U.S. Pat. No. 6,471,703 to Ashman, the contents of each patent reference hereby incorporated by reference in its entirety.

Figure 4:
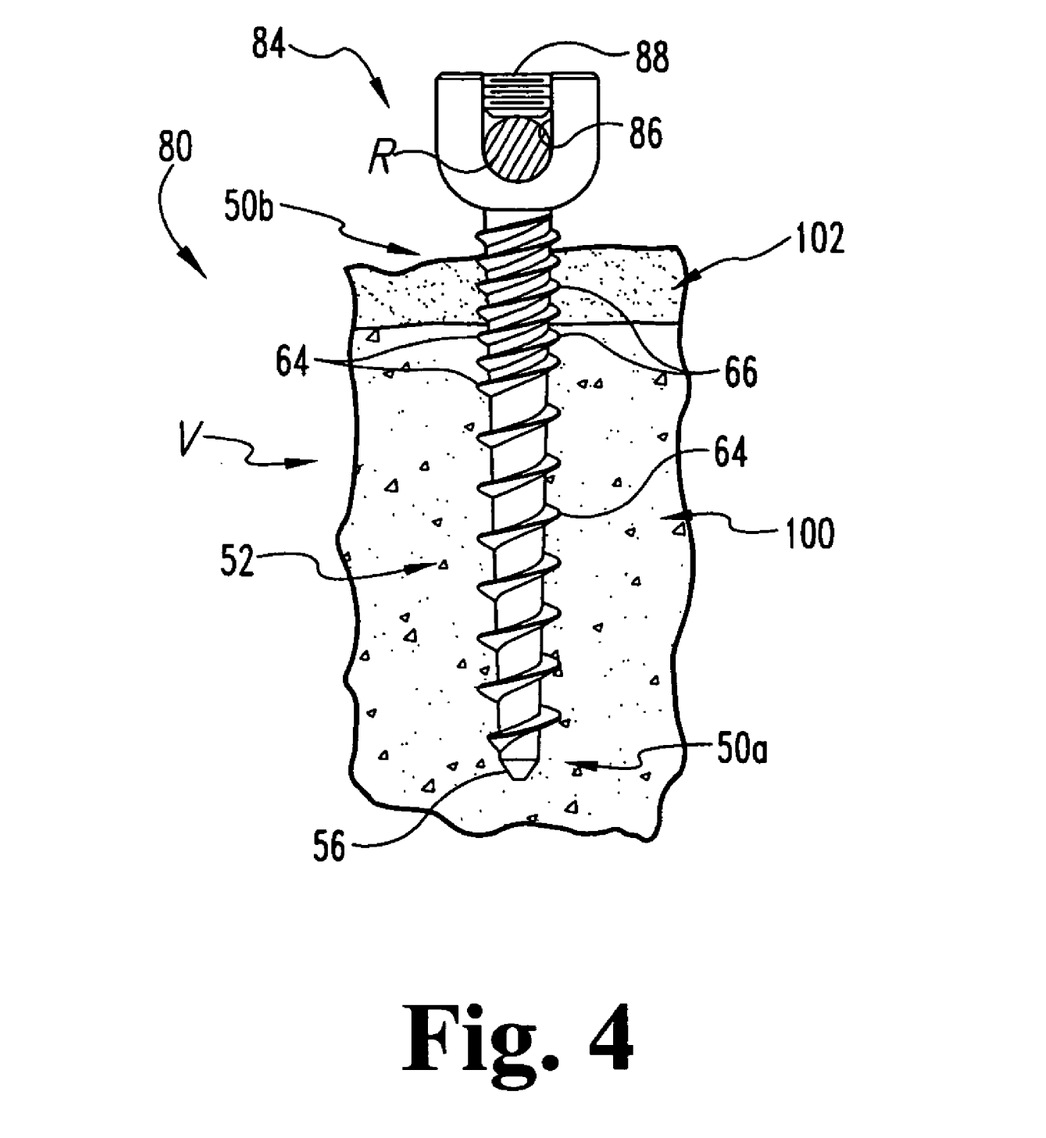
FIG. 4 is an elevational side view of a bone screw according to another form of the present invention, as engaged to bone and as coupled to a spinal rod.

Referring to FIG. 4, shown therein is a bone screw 80 according to another form of the invention for coupling with a spinal rod R. Specifically, the bone screw 80 includes a threaded shank 52 and a head 84 that is adapted for coupling with a spinal rod R. The threaded shank 52 is identical to that described above and illustrated in FIGS. 2 and 3. However, the bone screw head 84 defines a U-shaped channel 86 that is sized to receive the spinal rod R therein, with the spinal rod R captured within the channel 86 via a fastener or set screw 88 engaged with the bone screw head 84.

Figure 5:
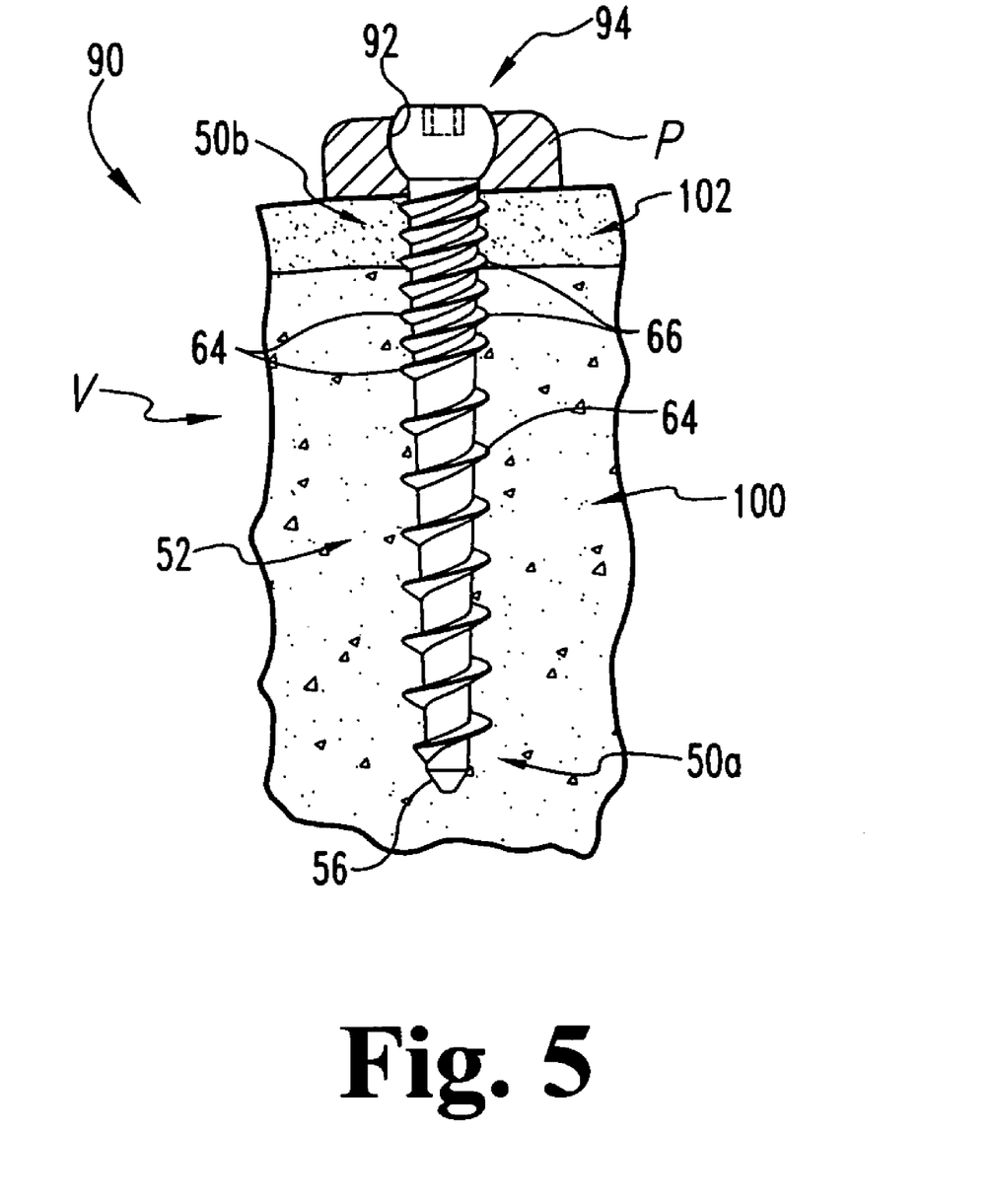
FIG. 5 is an elevational side view of a bone screw according to another form of the present invention, as engaged to bone and as coupled to a spinal plate.

Referring to FIG. 5, shown therein is a bone screw 90 according to another form of the invention which is adapted for coupling with an implant, such as a spinal plate P. In one embodiment, the spinal plate P includes one or more openings 92 for receiving one or more of the bone screws 90, with the bone screw 90 including an enlarged head portion 94. In the illustrated embodiment, the opening 92 includes a lower portion sized to receive the threaded shank 52 therethrough, and an upper portion sized to receive the enlarged bone screw head 94. As should be appreciated, threading of the bone screw 90 into the bone compresses the spinal plate P against an outer surface of the bone, thereby capturing the spinal plate P between the enlarged head 94 and the outer surface of the bone.

Figure 6:
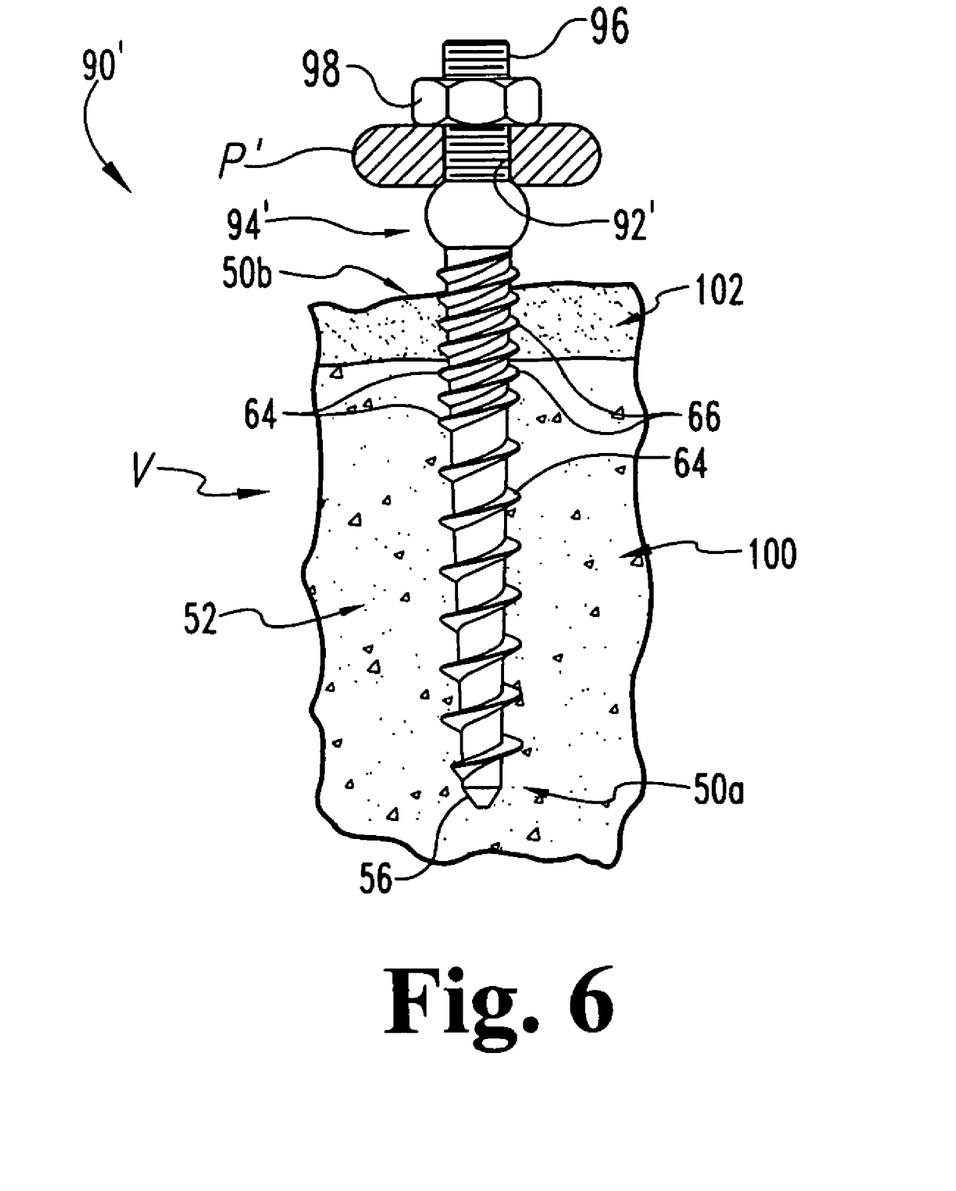
FIG. 6 is an elevational side view of a bone screw according to another form of the present invention, as engaged to bone and as coupled to a spinal plate.

Referring to FIG. 6, shown therein is a bone screw 90' according to a further form of the invention for coupling with a spinal plate P'. Specifically, the bone screw 90' includes a threaded shank 52, an enlarged head portion 94', and a threaded stem portion 96 extending from the enlarged head 94', with the spinal plate P' including one or more openings 92' for receiving the threaded stem portion 96 of one or more of the bone screws 90' therethrough, and with the spinal plate P' secured to the bone screw 90' via a lock nut 98 threaded onto the stem portion 96, thereby capturing the spinal plate P between the enlarged head 94' and the lock nut 98. As should be appreciated, the bone screw 90' illustrated in FIG. 6 allows the spinal plate P' to be spaced from the outer surface of the bone.

Having described the components and features associated with the present invention, reference will now be made to a method for engaging the bone screw to bone according to one form of the invention. As shown in FIGS. 3-6, in one embodiment, the bone comprises a vertebral body V having an inner cancellous bone region 100 and an outer cortical bone region 102. As discussed above, the outer cortical bone region 102 of the vertebral body V is relatively harder and denser compared to the inner cancellous bone region 100. The threaded shank 52 of the bone screw is driven into engagement with the vertebral body V, with the first threaded section 60 including the single lead threading 64 engaged within the inner cancellous bone region 100, and with the relatively finer second threaded section 62 including the dual lead threading 66 engaged within the outer cortical bone region 102.

As should be appreciated, the relatively course single lead threading 64 provides increased bone purchase capabilities and desirable pullout characteristics compared to the finer dual lead threading 66, which is particularly advantageous for anchoring within soft cancellous bone. As should be further appreciated, the relatively fine dual lead threading 66 provides increased fixation strength and stability compared to the courser single lead threading 64, which is particularly advantageous for fixation within relatively harder and denser cortical bone. Additionally, since the single lead threading 64 and the dual lead threading 66 each have substantially equal thread pitches $p_1$, $p_2$, threading of the second threaded section 62 into the cortical bone 102 will not require any additional turns relative to threading of the first threaded section 60 into the cancellous bone 100 to fully engage the bone screw within the vertebral body V. As should be appreciated a spinal implant such as a rod or plate may be coupled to one or more bone screws which are in turn anchored to corresponding vertebral bodies V for treatment of the spinal column.

It should be understood that the bone screws of the present invention may be anchored within any number of vertebral bodies V, including a single vertebral body or two or more vertebral bodies. In one embodiment of the invention, the bone screws are anchored within the pedicle region of a vertebral body. However, it should be understood that the bone screws may be anchored to other portions or regions of a vertebral body. It should also be understood that the bone screws of the present invention may be anchored to a posterior, anterior, lateral, posterolateral or anterolateral aspect of the vertebral body V. It should further be understood that the bone screws of the present invention may be attached to any region of the spinal column, including the cervical, thoracic, or lumbar regions of spinal column. It should likewise be understood that the bone screws of the present invention may be attached to bone structures other than vertebral bodies, such as, for example, bones associated with the arm or leg.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A bone screw, comprising:
a threaded shank including a distal end portion and a proximal end portion, said threaded shank defining a first threaded section extending from said distal end portion toward said proximal end portion and adapted for anchoring in cancellous bone, said threaded shank defining a second threaded section extending contiguously from said first threaded section toward said proximal end portion and adapted for engagement in cortical bone, said second threaded section comprising a finer thread pattern relative to said first threaded section, and wherein said threaded shank defines an inner thread root diameter that uniformly increases along a first portion of said first threaded section from a location adjacent said distal end portion to a mid-section of said threaded shank and uniformly increases along a second portion of said second threaded section from said mid-section to a location adjacent said proximal end portion, said first and second threaded sections extend substantially continuously and contiguously along a length of said threaded shank portion; and
wherein said threaded shank includes a first threading extending from said distal end portion toward said proximal end portion and including a single helical thread pattern defining said first threaded section for anchoring in the cancellous bone, said threaded shank including a second threading cooperating with said first threading to provide a double helical thread pattern defining said second threaded section for engagement in the cortical bone, and wherein said first threading has a first thread pitch, said second threading having a second thread pitch substantially equal to said first thread pitch.

2. The bone screw of claim 1, wherein said second threading is interleaved with and substantially centered between said first threading to provide said double helical thread pattern.

3. The bone screw of claim 1, wherein said second threading is offset about 180 degrees relative to said first threading.

4. The bone screw of claim 3, wherein said second threading is interleaved with and substantially centered between said first threading to define said double helical thread pattern for engagement in the cortical bone.

5. The bone screw of claim 3, wherein said first threaded section extends along at least about one half of said threaded shank.

6. The bone screw of claim 3, wherein said first threaded section extends along at least about two-thirds of said threaded shank.

7. The bone screw of claim 1, wherein said inner thread root diameter of said threaded shank uniformly increases between said distal end portion and said proximal end portion.

8. The bone screw of claim 7, wherein said inner thread root diameter increases by at least about 25% between said distal end portion and said proximal end portion.

9. The bone screw of claim 7, wherein said outer thread diameter adjacent said distal end portion is at least about 25% greater than said inner thread diameter adjacent said distal end portion.

10. The bone screw of claim 1, wherein said inner thread root diameter increases along an entire length of said threaded shank.

11. The bone screw of claim 1, wherein said first thread pitch is at least as large as said inner thread root diameter adjacent said distal end portion.

12. The bone screw of claim 11, wherein said first thread pitch is at least as large as said inner thread root diameter along an entire length of said threaded shank.

13. The bone screw of claim 1, further comprising a head portion extending from said proximal end portion of said threaded shank; and
a spinal implant coupled to said head portion of said bone screw.

14. The spinal system of claim 13, wherein said spinal implant comprises one of a spinal rod and a spinal plate.

15. The bone screw of claim 1, wherein said first thread pitch and said second thread pitch are constant.

16. The bone screw of claim 1, wherein said inner thread root diameter increases from a first root diameter adjacent said distal end portion to a larger second root diameter defined by said mid-section of said threaded shank, and increases from said second root diameter defined by said mid-section to a larger third root diameter adjacent said proximal end portion.

17. The bone screw of claim 1, further comprising:
a screw head portion extend from said threaded shank, said screw head portion comprising an unthreaded and relatively smooth stem portion having a substantially uniform outer diameter from said proximal end portion of said threaded shank to a proximal-most end of the bone screw; and
a spinal implant connected to said stem portion.

18. A bone screw, comprising:
a threaded shank including a distal end portion and a proximal end portion, said threaded shank defining a first threaded section extending from said distal end portion toward said proximal end portion and adapted for anchoring in cancellous bone, said threaded shank defining a second threaded section extending contiguously from said first threaded section toward said proximal end portion and adapted for engagement in cortical bone, said second threaded section comprising a finer thread pattern relative to said first threaded section, and wherein said threaded shank defines an inner thread root diameter that uniformly increases along a first portion of said first threaded section from a location adjacent said distal end portion to a mid-section of said threaded shank and uniformly increases along a second portion of said second threaded section from said mid-section to a location adjacent said proximal end portion, said first and second threaded sections extend substantially continuously and contiguously along a length of said threaded shank portion; and
wherein said threaded shank includes a first helical threading extending from said distal end portion toward said proximal end portion to define said first threaded section for anchoring in the cancellous bone, said threaded shank including a second helical threading interleaved with and substantially centered between said first helical threading to define said second threaded section for engagement in the cortical bone, each of said first and second helical threadings having a substantially equal thread pitch, and wherein said first threaded section extends along at least about two-thirds of said threaded shank.

19. The bone screw of claim 18, wherein said second helical threading is offset about 180 degrees relative to said first helical threading to define said second threaded section for engagement in the cortical bone.

20. The bone screw of claim 18, further comprising a head portion extending from said proximal end portion of said threaded shank, said head portion adapted for coupling to an elongate member that is sized and configured to extend between at least two adjacent vertebrae.

21. The bone screw of claim 18, wherein said inner thread root diameter uniformly increases from said distal end portion to said proximal end portion.

22. The bone screw of claim 18, wherein said thread pitch is at least as large as said inner thread root diameter defined by said first threaded section adjacent said distal end portion.

23. The bone screw of claim 22, wherein said thread pitch is at least as large as said inner thread root diameter along an entire length of said first threaded section.

24. The bone screw of claim 22, wherein said thread pitch is at least as large as said inner thread root diameter along an entire length of said threaded shank.

25. The bone screw of claim 18, wherein said thread pitch is constant.

26. The bone screw of claim 18, wherein said inner thread root diameter increases from a first root diameter adjacent said distal end portion to a larger second root diameter defined by said mid-section of said threaded shank, and increases from said second root diameter defined by said mid-section to a larger third root diameter adjacent said proximal end portion.

27. The bone screw of claim 18, further comprising:
a screw head portion extend from said threaded shank, said screw head portion comprising an unthreaded and relatively smooth stem portion having a substantially uniform outer diameter from said proximal end portion of said threaded shank to a proximal-most end of the bone screw; and
a spinal implant connected to said stem portion.

28. A bone screw, comprising:
a threaded shank including a distal end portion and a proximal end portion, said threaded shank defining a first threaded section extending from said distal end portion toward said proximal end portion and adapted for anchoring in cancellous bone, said threaded shank defining a second threaded section extending contiguously from said first threaded section toward said proximal end portion and adapted for engagement in cortical bone, said second threaded section comprising a finer thread pattern relative to said first threaded section, and wherein said threaded shank defines an inner thread root diameter that uniformly increases along a first portion of said first threaded section from a location adjacent said distal end portion to a mid-section of said threaded shank and uniformly increases along a second portion of said second threaded section from said mid-section to a location adjacent said proximal end portion, said first and second threaded sections extend substantially continuously and contiguously along a length of said threaded shank portion; and
wherein said threaded shank includes a first threading extending from said distal end portion toward said proximal end portion and including a single helical thread pattern defining said first threaded section for anchoring in the cancellous bone, said threaded shank including a second threading cooperating with said first threading to provide a double helical thread pattern defining said second threaded section for engagement in the cortical bone, and wherein said first threading has a first thread pitch, said second threading having a second thread pitch substantially equal to said first thread pitch; and wherein said first and second threaded sections of said threaded shank define a uniform outer thread diameter from a point adjacent said distal end portion and along said mid-section to said proximal end portion.

29. The bone screw of claim 28, wherein said inner thread root diameter increases from a first root diameter adjacent said distal end portion to a larger second root diameter defined by said mid-section of said threaded shank, and increases from said second root diameter defined by said mid-section to a larger third root diameter adjacent said proximal end portion.

30. The bone screw of claim 28, further comprising:
a screw head portion extend from said threaded shank, said screw head portion comprising an unthreaded and relatively smooth stem portion having a substantially uniform outer diameter from said proximal end portion of said threaded shank to a proximal-most end of the bone screw; and
a spinal implant connected to said stem portion.

31. A bone screw, comprising:
a threaded shank including a distal end portion and a proximal end portion, said threaded shank including a first helical threading extending from said distal end portion toward said proximal end portion and defining a single lead thread pattern adapted for anchoring in cancellous bone, said threaded shank including a second helical threading interleaved with said first threading to define a duel lead thread pattern adjacent said proximal end portion of said threaded shank adapted for engagement in cortical bone, and wherein said first and second helical threadings of said threaded shank define an inner thread root diameter that increases along a first portion of said first threaded section from a location adjacent said distal end portion to a mid-section of said threaded shank and increases along a second portion of said second threaded section from said mid-section toward said proximal end portion, said first and second helical threadings extend substantially continuously and contiguously along a length of said threaded shank portion, and wherein said first helical threading has a first thread pitch, said second helical threading having a second thread pitch substantially equal to said first thread pitch.

32. The spinal system of claim 31, wherein said second helical threading is substantially centered between said first helical threading to define said dual lead thread pattern for engagement in the cortical bone.

33. The spinal system of claim 31, wherein said second helical threading is offset about 180 degrees relative to said first helical threading to define said dual lead thread pattern for engagement in the cortical bone.

34. The bone screw of claim 31, wherein said second helical threading is offset about 180 degrees relative to said first helical threading.

35. The bone screw of claim 31, wherein said a single lead thread pattern extends along at least about two-thirds of said threaded shank.

36. The bone screw of claim 31, wherein said inner thread root diameter increases along an entire length of said threaded shank.

37. The bone screw of claim 31, wherein said first and second helical threadings of said threaded shank define a uniform outer thread diameter from a point adjacent said distal end portion and along said mid-section to said proximal end portion.

38. The bone screw of claim 31, wherein said first helical threading has a thread pitch, said thread pitch being at least as large as said inner thread root diameter defined by said first helical threading adjacent said distal end portion.

39. The bone screw of claim 31, wherein said inner thread root diameter increases from a first root diameter adjacent said distal end portion to a larger second root diameter defined by said mid-section of said threaded shank, and increases from said second root diameter defined by said mid-section to a larger third root diameter adjacent said proximal end portion.

40. The bone screw of claim 31, further comprising:
a screw head portion extend from said threaded shank, said screw head portion comprising an unthreaded and relatively smooth stem portion having a substantially uniform outer diameter from said proximal end portion of said threaded shank to a proximal-most end of the bone screw; and
a spinal implant connected to said stem portion.

* * * * *